(12) United States Patent
Akdeniz et al.

(10) Patent No.: US 7,698,949 B2
(45) Date of Patent: Apr. 20, 2010

(54) ACTIVE WASHERS FOR MONITORING BOLTED JOINTS

(75) Inventors: Aydin Akdeniz, Redmond, WA (US); Jeffrey R. Kollgaard, Kent, WA (US); Matthew C. Malkin, Seattle, WA (US)

(73) Assignee: The Boeing Company, Chicago, IL (US)

( * ) Notice: Subject to any disclaimer, the term of this patent is extended or adjusted under 35 U.S.C. 154(b) by 888 days.

(21) Appl. No.: 11/222,720

(22) Filed: Sep. 9, 2005

(65) Prior Publication Data
US 2007/0056375 A1 Mar. 15, 2007

(51) Int. Cl.
G01H 11/08 (2006.01)
H01L 41/00 (2006.01)

(52) U.S. Cl. .................. 73/649; 73/632; 73/761; 310/322

(58) Field of Classification Search ............ 73/649, 73/761, 768, 774, 775, 862.04, 862.68, 862.54–862.56, 73/632; 310/322
See application file for complete search history.

(56) References Cited

U.S. PATENT DOCUMENTS

| | | | |
|---|---|---|---|
| 4,079,624 A | | 3/1978 | Kurtz |
| 4,295,377 A | | 10/1981 | Couchman |
| 4,342,233 A | * | 8/1982 | Edmondson et al. ...... 73/862.06 |
| 4,706,387 A | * | 11/1987 | Wichorek .................. 33/786 |
| 4,773,272 A | * | 9/1988 | Trungold ..................... 73/761 |
| 4,846,001 A | | 7/1989 | Kibblewhite |
| 4,899,591 A | | 2/1990 | Kibblewhite |
| 5,029,480 A | | 7/1991 | Kibblewhite |
| 5,131,276 A | | 7/1992 | Kibblewhite |
| 5,205,176 A | | 4/1993 | Kibblewhite |
| 5,220,839 A | | 6/1993 | Kibblewhite |
| 5,222,399 A | * | 6/1993 | Kropp ..................... 73/862.68 |
| 5,379,647 A | * | 1/1995 | Sherwin ................... 73/834 |
| 5,437,525 A | | 8/1995 | Bras |

(Continued)

FOREIGN PATENT DOCUMENTS

EP 0 381 791 B1 4/1994

(Continued)

OTHER PUBLICATIONS

Smart Technologies for Bolted Joint in civil system, 2nd workshop on mitigation of Earthquake Disaster by Advanced Technology, Nov. 29-30, 2000, Las Vegas.*

(Continued)

Primary Examiner—J M Saint Surin
(74) Attorney, Agent, or Firm—Alston & Bird LLP

(57) ABSTRACT

Apparatus, systems, and methods for inspecting and monitoring bolted joints of metallic and composite structures for defects such as delamination and fatigue cracking are provided that incorporate ultrasonic transducers with load bearing washers. These active washers may be used for inspecting and monitoring a structure beneath such load bearing fasteners as bolts and nuts. Active washers may be used for continuous, periodic, and controlled inspections of bolted joints. Ultrasonic transducers may be permanently applied to a surface of a washer or recessed in a cavity on a surface of the washer. Inspection signals may be transmitted from ultrasonic transducers into a structure and reflected in pulse-echo application or received by another active washer on the opposing side of the structure in a through-transmission application.

25 Claims, 4 Drawing Sheets

U.S. PATENT DOCUMENTS

| | | | |
|---|---|---|---|
| 5,721,380 | A | 2/1998 | Gozlan |
| 5,798,599 | A * | 8/1998 | Harwood ............... 310/323.01 |
| 6,009,759 | A | 1/2000 | Kibblewhite et al. |
| 6,099,223 | A * | 8/2000 | Galis et al. .................. 411/538 |
| 6,285,034 | B1 * | 9/2001 | Hanna et al. ............. 250/559.2 |
| 6,715,365 | B2 | 4/2004 | Davey |
| 6,733,456 | B1 | 5/2004 | Suorsa et al. |
| 6,784,662 | B2 | 8/2004 | Schlicker et al. |
| 6,990,866 | B2 * | 1/2006 | Kibblewhite ................ 73/761 |
| 7,111,498 | B2 * | 9/2006 | Jin .............................. 73/49.1 |
| 7,117,742 | B2 | 10/2006 | Kim |
| 7,242,299 | B2 * | 7/2007 | Kelsch et al. ............ 340/568.1 |
| 7,325,456 | B2 * | 2/2008 | Kim ............................. 73/587 |
| 7,467,556 | B2 * | 12/2008 | Kibblewhite et al. .......... 73/761 |
| 7,528,598 | B2 * | 5/2009 | Goldfine et al. ............. 324/240 |
| 2004/0025595 | A1 | 2/2004 | Brennan |
| 2004/0065154 | A1 | 4/2004 | Kibblewhite |
| 2005/0007106 | A1 | 1/2005 | Goldfine et al. |
| 2007/0007955 | A1 * | 1/2007 | Goldfine et al. ............. 324/240 |
| 2008/0258720 | A1 | 10/2008 | Goldfine et al. |

FOREIGN PATENT DOCUMENTS

| | | | |
|---|---|---|---|
| WO | WO/0050803 | * | 8/2000 |
| WO | WO 2004/027271 A2 | | 4/2004 |

OTHER PUBLICATIONS

Detection of bolt loosening in C-C compodite thermal protection panels: Experimental verification, 2006 Smart Mater.Struct 15 591.*

*Electromagnetic Smart Washer for Detecting Bolthole Cracking*, available at http://www.nasatech.com/Briefs/May98/MFS26479.html, (Mar. 31, 2005), 2 pages.

*SBIR 95-1 Solicitation, Project Summary*, available at http://www.spacepda.net/abstracts/95/sbir_html/951449.html, (Mar. 31, 2005), 2 pages.

Goldfine, N. et al., "Material Condition and Usage Monitoring Sensors and Algorithms for Adaptive Management of Legacy and New Platforms", *Jentek Sensors*, 11 pages.

Barton, "Comparative Vacuum Monitoring: a New Method of In-Situ Real-Time Crack Detection and Monitoring", 9 pages.

*The permanently mounted durable thin-film transducer*, PFW Technologies, available at http://www.pfw-tec.com/images/duennschicht_e_gr.gif, (Mar. 31, 2005), 1 page.

*Sputtering applies a permanent piezoelectric thin-layer to the bolt*, PFW Technologies, available at http://www.pfw-tec.com/en/svs2.htm, (Mar. 31, 2005), 1 page.

*Method of measuring load*, PFW Technologies, available at http://www.pfw-tec.com/images/vorspann_e_gr.gif, (Mar. 31, 2005), 1 page.

*Permanent Mounted Transducer System The system for safe bolted joints*, PFW Technologies, available at http://www.pft-tec.com/en/sys1a.htm, (Mar. 31, 2005), 1 page.

*We are closing the confidence gap*, PFW Technologies, available at http://www.pfw-tec.com/en/untern.htm, (Mar. 31, 2005), 1 page.

*PMT System is suitable for both small series and automated bolt assembly*, PFW Technologies, available at http://www.pfw-tec.com/en/sys3a.htm, (Mar. 31, 2005), 1 page.

Giurgiutiu, V. et al., "New Results in the Application of E/M Impedance Method to Machinery Health Monitoring and Failure Prevention", $53^{rd}$ *Meeting of the Society for Machinery Failure Prevention Technology*, Apr. 20-22, 1999, 9 pages.

*Piezoelectric Transducers*, available at http://www.ndt-ed.org/EducationResources/CommunityCollege/Ultrasonics/EquipmentTrans/piez . . . , (Mar. 31, 2005), 2 pages.

U.S. Appl. No. 60/473,180, filed May 23, 2003; in re: Goldfine; entitled: *Hybrid Wound/Etched Winding Constructs*.

U.S. Appl. No. 60/693,347, filed Jun. 22, 2005; in re: Goldfine; entitled: *Fastener/Fitting Based Sensing Systems*.

U.S. Appl. No. 60/696,625, filed Jul. 5, 2005; in re: Goldfine; entitled: *Quality Assessment of Ceramic Matrix Composites*.

* cited by examiner

ACTIVE WASHERS FOR MONITORING BOLTED JOINTS

FIELD OF THE INVENTION

The present invention relates generally to an apparatus, systems, and methods for inspecting a structure and, more particularly, to an apparatus, systems, and methods for using active washers for non-destructive inspection of bolted joints of a structure.

BACKGROUND

Structural inspections represent a large portion of overall maintenance costs on aircraft and other vehicles and structures. Non-destructive inspection (NDI) of structures involves thoroughly examining a structure without harming the structure or requiring its significant disassembly. Non-destructive inspection is often preferred over visual or destructive inspection methods to avoid the schedule, labor, and costs associated with removal of parts or other disassembly for inspection (with the associated potential for damaging the structure). In the field, access to interior surfaces of the structure is often restricted, requiring disassembly of the structure, introducing additional time and labor. Frequently, inspections are necessary or mandated to be performed in hazardous or difficult-to-access areas, such as in fuel cells, electronics bays, and pressure bulkhead cavities, which may require fuel cell venting and removal of panels, ducts, insulation, and other surrounding structures. Non-destructive inspection is advantageous for many applications in which a thorough inspection of the exterior and/or interior of a structure is required, particularly where gaining access to an inspection area is limited. For example, non-destructive inspection is commonly used in the aircraft industry to inspect aircraft structures for damage or defects (flaws) in the structure. Inspection may be performed during manufacturing or after the completed structure has been put into service to validate the integrity and fitness of the structure.

Related to the need for performing structural inspections is the ability to determine whether maintenance is required. For example, to decrease the costs of airplane maintenance, the concept of Vehicle Health Management (VHM) can be used to more accurately determine when maintenance is required, in essence by monitoring the health of the vehicle. Central to the concept of Vehicle Health Management for an airplane is a network of sensors installed throughout the airplane. These sensors may be monitored continuously or queried periodically during maintenance checks, when the tools and/or facilities for repairing any problems are immediately available. Such a sensor network may also be used for Condition-Based Maintenance (CBM) in which maintenance checks and maintenance of parts and systems of a vehicle may be initiated by sensor data. For example, maintenance intervals of airplanes are typically conservatively set for routine maintenance, but Condition-Based Maintenance could reduce the need for certain routine maintenance which can be monitored to determine when the maintenance is required, thereby resulting in less frequent maintenance and reduced maintenance overall.

A feature of airplanes and other vehicles and structures that is critical to structural integrity is the bolted joint, including the bolted composite joint. Of concern for bolted composite joints is the potential for defects such as delamination and fatigue cracking around the bolt-holes. Currently, one approach for inspecting bolted joints involves an operator gaining access to an inspection area around the bolted joint and inspecting the area immediately surrounding the bolt-hole with a shear wave ultrasonic beam or eddy current. The operator typically scans the inspection area while monitoring a display screen for any signals which may be interpreted as a defect in the structure. Such inspection often requires preparing the inspection area surface, such as scraping away sealant fillets to provide a clean surface for a transducer or probe. Gaining access to the inspection area often involves removing access panels, hydraulic lines, cables, hoses, brackets, and other interfering structures. In addition to the practical impediments to such inspection, the operator must know how to place and orient a transducer or probe to ensure that defects are examined from the optimum angle. Further, the operator must be able to interpret and evaluate the inspection data on the display in real-time and determine if any potential defects are significant or non-significant. Following such inspections, sealants and coatings must be restored and interfering structures replaced.

Manual inspection of structures typically is very labor intensive, time consuming, and expensive. Manual inspection is subject to human error in performance and variations of interpretation of results. Noise in inspection signals can be interpreted as defects (false positives), and defects can be missed or overlooked as non-significant (false negatives). Further, shear wave ultrasonic beam and eddy current inspection are limited in that only cracks of particular orientations may be detectable. Many structures may also incorporate numerous bolted joints which require inspection in areas which cannot be accessed or are exceptionally difficult to access.

Several approaches have been attempted to inspect bolted joints with sensors. One approach is a smart washer proposed by Innovative Dynamics, Inc, of Ithaca, N.Y. These smart washers incorporate eddy current sensors. However, the sensors cannot be "nulled" or balanced between widely spaced interrogation intervals, so it is not possible to discern crack signals from signals caused by temperature variations, instrument drift, and other noise factors. Furthermore, these smart washers use eddy currents and can only be used on electrically conductive structures.

Another approach is using eddy current rosettes produced by Jentek Sensors of Waltham, Mass. These eddy current rosettes are bonded onto the area surrounding a rivet or bolt. The rosettes contain eddy current sensor loops for detection of surface-breaking cracks. The rosettes can be calibrated in air and provide an absolute measurement, unlike the Innovative Dynamics smart washers which only provide relative measurements that depend upon a stable null point over time. However, the Jentek Sensors rosettes depend on a strain gage adhesive to cement the sensor in place, and these adhesives are subject to failure over time. Furthermore, the Jentek Sensors rosettes are expensive, can be difficult to use and understand, and require new computer models for different applications.

Yet another approach is comparative vacuum monitoring (CVM) sensors produced by Structural Monitoring Systems Ltd. of Perth, Australia. Comparative vacuum monitoring sensors measure the pressure differential between small recesses containing a low vacuum alternating with small recesses at atmosphere, where the alternating series of low vacuum and atmosphere recesses are located in a simple manifold. If no surface-breaking crack is present, the low vacuum will remain at a stable level. If a crack develops, air will flow through the crack from the atmosphere recesses to the vacuum recesses. Comparative vacuum monitoring sensors only have application to surface-breaking fatigue cracks and are unable to detect delaminations below the surface, or fatigue cracks originating at the far surface of a layer.

Although used for a different purpose, a related technology is the permanent mounted transducer (PMT) system by PFW Technologies GmbH of Speyer, Germany. The PFW Technologies permanent mounted transducer system uses an ultrasonic transducer with a bolt to measure elongations of the bolt caused by the clamp load on the bolt, thereby providing a way of measuring the clamp load on the bolt during assembly and providing a way of controlling the torque load exerted by a tightening tool. The PFW Technologies permanent mounted transducer system, however, does not have the capability of detecting defects in the vicinity of the bolt-hole, but only monitors changes in the bolt stress state.

Accordingly, improved apparatus, systems, and methods for inspecting bolted joints of structures are desired.

BRIEF SUMMARY OF THE INVENTION

Provided are improved apparatus, systems, and methods for inspecting and monitoring bolted joints of both metallic and composite structures for defects such as delamination and fatigue cracking.

Embodiments of apparatus of the present invention use one or more inspection sensors, typically ultrasonic transducers, incorporated with or into washers, typical of washers used as a bearing surface beneath a nut or bolt head, creating what are referred to herein as active washers. Active washers may be used to inspect and monitor structures under washers used with bolts, nuts, rivets, and similar bearing fasteners. Active washers may be used for continuous, periodic, and controlled inspections of bolted joints. Active washers may be used individually for inspection of a bolted joint and used as sensors of a Vehicle Health Management system. Using active washers may reduce maintenance costs and overall required maintenance by providing a way of passively inspecting and monitoring bolted joints to determine whether maintenance is required or not. Use of active washers eliminates the need for disassembly and related labor intensive activities associated with gaining access to inspection areas and performing manual inspections. Instead, active washers may remotely provide inspection and monitoring data.

Embodiments of methods of the present invention provide an active washer with an inspection sensor carried by the washer which is around a bolted joint such that the inspection sensor is capable of inspecting at least a portion of the structure proximate to the washer. An inspection signal may be transmitted from the inspection sensor into the structure, and an inspection signal may be received from the structure, either in a pulse-echo mode of non-destructive inspection by the inspection sensor transmitting the inspection signal into the structure, or in a through-transmission mode of non-destructive inspection by another inspection sensor on the opposing side of the structure from the first washer.

These and other characteristics, as well as additional details, of the present invention are further described in the Detailed Description.

BRIEF DESCRIPTION OF THE DRAWING(S)

Having thus described the invention in general terms, reference will now be made to the accompanying drawings, which are not necessarily drawn to scale, and wherein:

DETAILED DESCRIPTION

Figure 1:
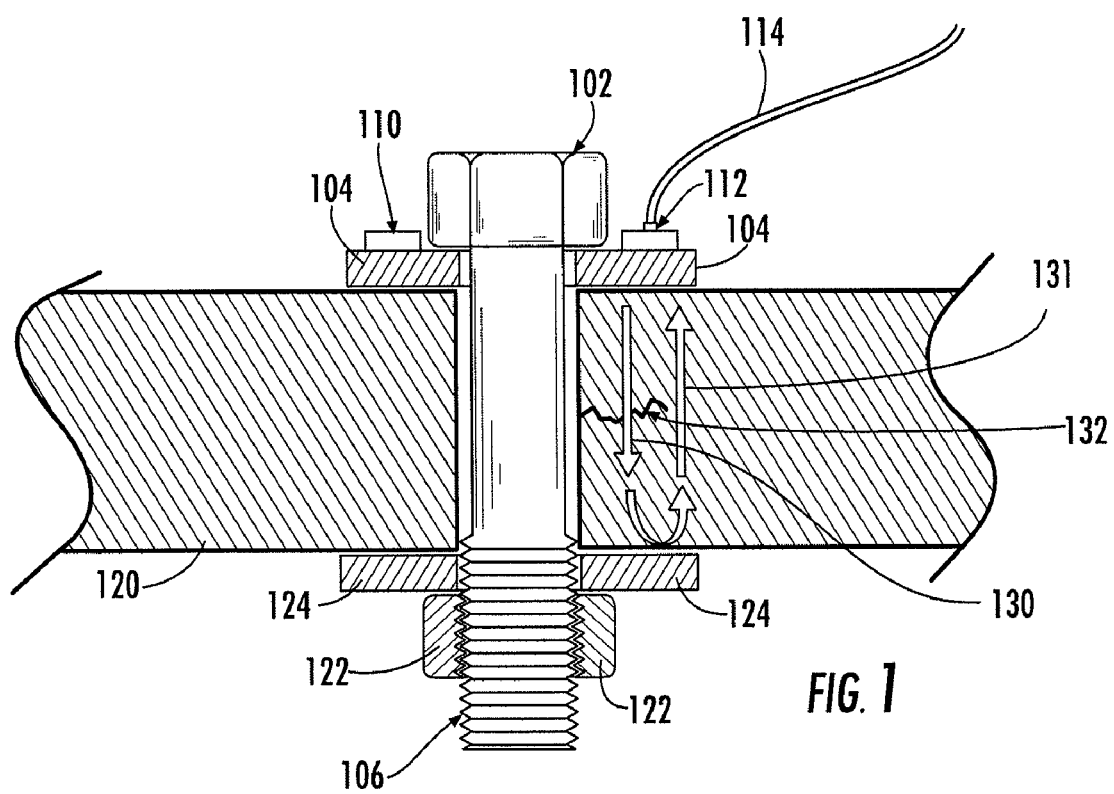
FIG. 1 is a cross-sectional schematic diagram of an embodiment of the present invention.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The term "bolted joint" refers generally to a joint which is held together using a bolt and a nut or similar fastener on opposite sides of a structure, where the bolt passes through a bolt-hole in the structure. As used herein, a bolt also refers to similar fastening mechanisms which rely upon a connector passing through a hole in a structure and having expanded surfaces functioning like a bolt head and a nut on opposing sides of a structure. The bolted structure may be a single layer, or have multiple layers jointed together. However, for simplicity, embodiments of the present invention are generally described below with reference to typical bolted joints using a bolt and a nut, but embodiments of the present invention are not limited to configurations of bolted joints only using bolts and nuts.

Although embodiments of the present invention may be used for applications in the aircraft industry, the present invention is applicable to inspecting and monitoring other bolted joints, and may be advantageously used, without limitation, for inspecting and monitoring bolted joints on holding tanks and pipelines. Similarly, although embodiments of the present invention are described with reference to use of ultrasonic transducers, other types of inspection sensors may be used with embodiments of the present invention.

Embodiments of the present invention incorporate a non-destructive inspection sensor with or into a washer, typical of washers used as a bearing surface beneath a nut or bolt head, creating what are referred to herein as "active washers." The non-destructive inspection sensor may be incorporated as part of the washer, for example, using sensor mounting techniques such as used by PFW Technologies for creating a permanent mounted transducer (PMT) system of a bolt as described in U.S. Pat. No. 4,846,001 and which is incorporated herein by reference, except that a non-destructive inspection sensor of an embodiment of the present invention is incorporated into a washer, rather than a bolt or other fastener adapted to be deformed, and is used for defect inspection of a bolted structure, rather than elongation of a bolt. Because the sensor of an active washer is typically permanently mounted or permanently fixed in place in a cavity or similar recess, a stable environment is created between multiple inspections. The stable environment enables previous inspection results to be retrieved and subtracted from current readings to isolate changes in the structure and identify changes due to progression or growth of defects, as explained further below.

Because an active washer is situated in close proximity to the bolt hole, an active washer may be able to detect cracks and delaminations at early stated of progression, when they might otherwise be hard to detect or undetectable by other inspection methods. Active washers may be most sensitive for detection of delaminations in composite bolted structures due to the orientation of laminar flaws with regard to the interrogating wave. However, detection of axial fatigue cracks is also possible by measuring diffraction signals from the crack tip and referencing the diffraction signals against signals taken during previous maintenance checks. By subtracting previous signals from later signals, the changes due to crack growth are isolated and the signal-to-noise level increases.

FIG. 1 is a cross-sectional schematic diagram of an embodiment of the present invention. FIG. 1 presents an example configuration for an active washer. The transducer 110 is mounted to the surface of the washer 104 facing away from the structure 120, typically where the transducer is permanently affixed to the washer, although embodiments of the present invention may use inspection sensors which are only carried by a washer, such as describe below with reference to FIGS. 2, 3, and 4 which show inspection sensors that may float in cavities defined in the washer. The transducer 110 is mounted radially from the center of the washer 104 just beyond where the head of the bolt 102 terminates. The fact that the washer 104 has additional width beyond the head of the bolt 102, over which the bearing load of the bolt 102 is dispersed, allows space for the transducer 110 on the top of the washer 104. Alternatively, if insufficient space is available to accommodate both the head of a bolt and a transducer, the transducer may be segmented and recessed into counterbore chambers occupying space beneath the bearing surface of the head of the bolt. If an active washer with the configuration shown in FIG. 1 is used in a pulse-echo inspection application, signal echoes from the far side of the washer may interfere with the interpretation of signal echoes originating beyond the washer in the structure under inspection. This would not be a problem, however, if the active washer were used in a through-transmission inspection application because stable, interfering signals would be subtracted out, i.e., each monitoring measurement would be the result of subtracting out the baseline signal so that only changes remain, such as changes produced by propagating damage.

The configuration in FIG. 1 also shows how the bolt 102 includes a shaft with threads 106 at the terminating end of the shaft opposite the head of the bolt 102. A nut 122 is screwed onto the threads 106 of the bolt 102 to tighten down the bolted joint. A second washer 124, which may also be an active washer, is located between the nut 122 and the structure 120. Accordingly, the bolted joint may resemble and function as conventional bolted joint, except that at least one washer used for displacing the bearing load of the fastener is an active washer. As shown in FIG. 1, an active washer may include a probe contact 112 for the transducer 110 to which a data connection can be made using a wire 114. A wired connection to an active washer can be connected to a data control system to inspect and monitor the bolted joint for the active washer, and potentially numerous active washers or similar inspection sensors as part of a Vehicle Health Management system. Embodiments of the present invention may also operate using wireless communications with active washers, although considerations such as space limitations and availability of a power source may restrict the use of wireless communications in some applications.

Figure 1A:
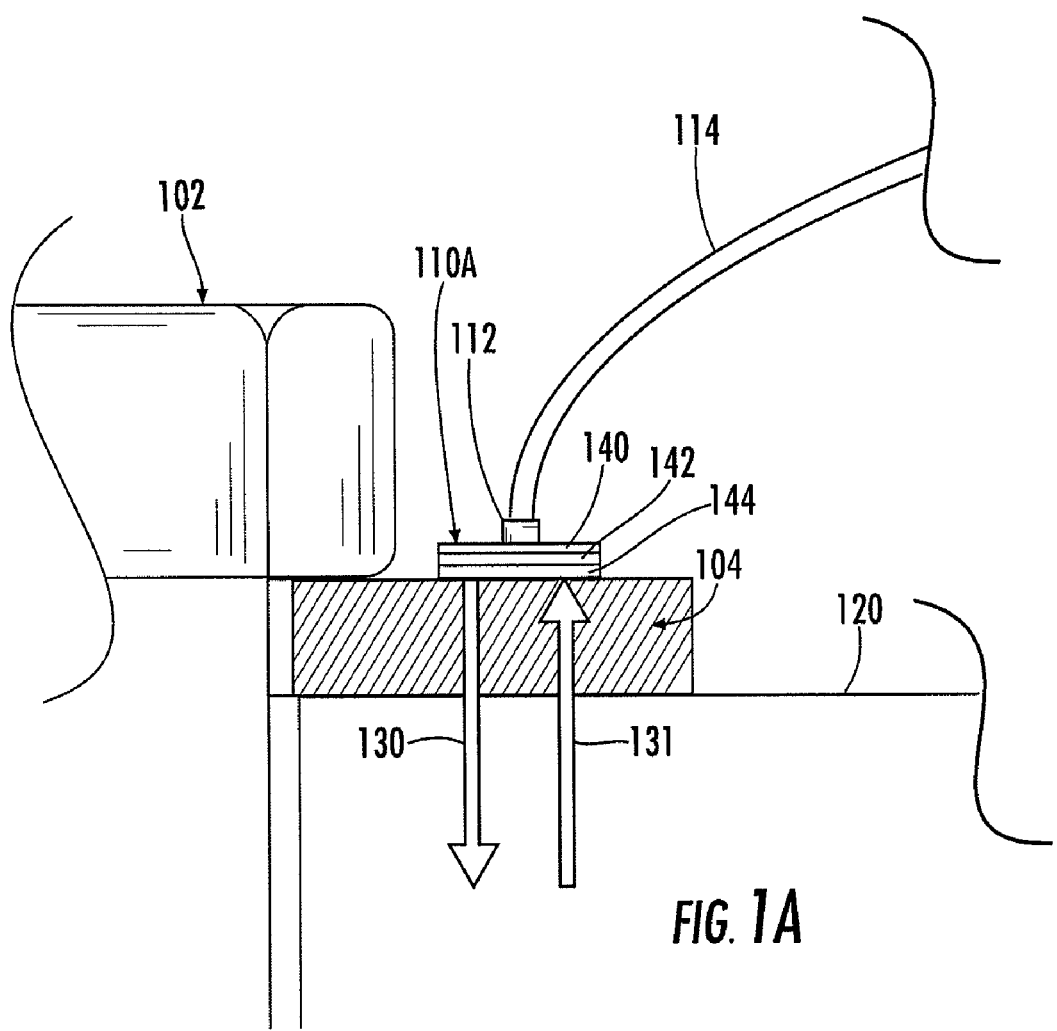
FIG. 1A is an enlarged view of a portion of FIG. 1.

FIG. 1A is an enlarged view of a portion of FIG. 1 showing the composition of an example embodiment of a transducer for an active washer. The example transducer 110A includes a probe contact 112 attached to a metal electrode layer 140 which is attached to a protection layer/corrosion barrier 142 which is attached to a piezoelectric thin-film ceramic crystal 144 which is attached to a washer 104. The metal electrode layer 140 and washer 104 operate as the two opposing poles for the piezoelectric crystal 144.

In an example operation of an embodiment of the present invention, non-destructive pulse-echo ultrasonic inspection may consist of making contact with two poles across a piezoelectric ultrasonic transducer crystal sensor bonded to the surface of a washer opposite the structure and exciting the crystal with a voltage spike, where one of the poles is the washer material itself, such as where the metal electrode layer 140 and the washer 104 are the poles for the transducer crystal. The voltage spike causes the sensor to launch an ultrasonic compression wave 130 through the washer and into the structure in contact with one face of the washer. As in conventional pulse-echo ultrasonic inspections, the ultrasonic wave launched into the base material may be reflected, and/or altered by flaws in the material and reflected by the far-side of the structure, and a return signal 131 may be detected by the sensor. The presence of a sealant (or couplant) between the washer and the structure may assist (couple) transmission of the ultrasonic wave into the structure, but the presence of a sealant (or couplant) is not necessary for operation of embodiments of the present invention.

Figure 2:
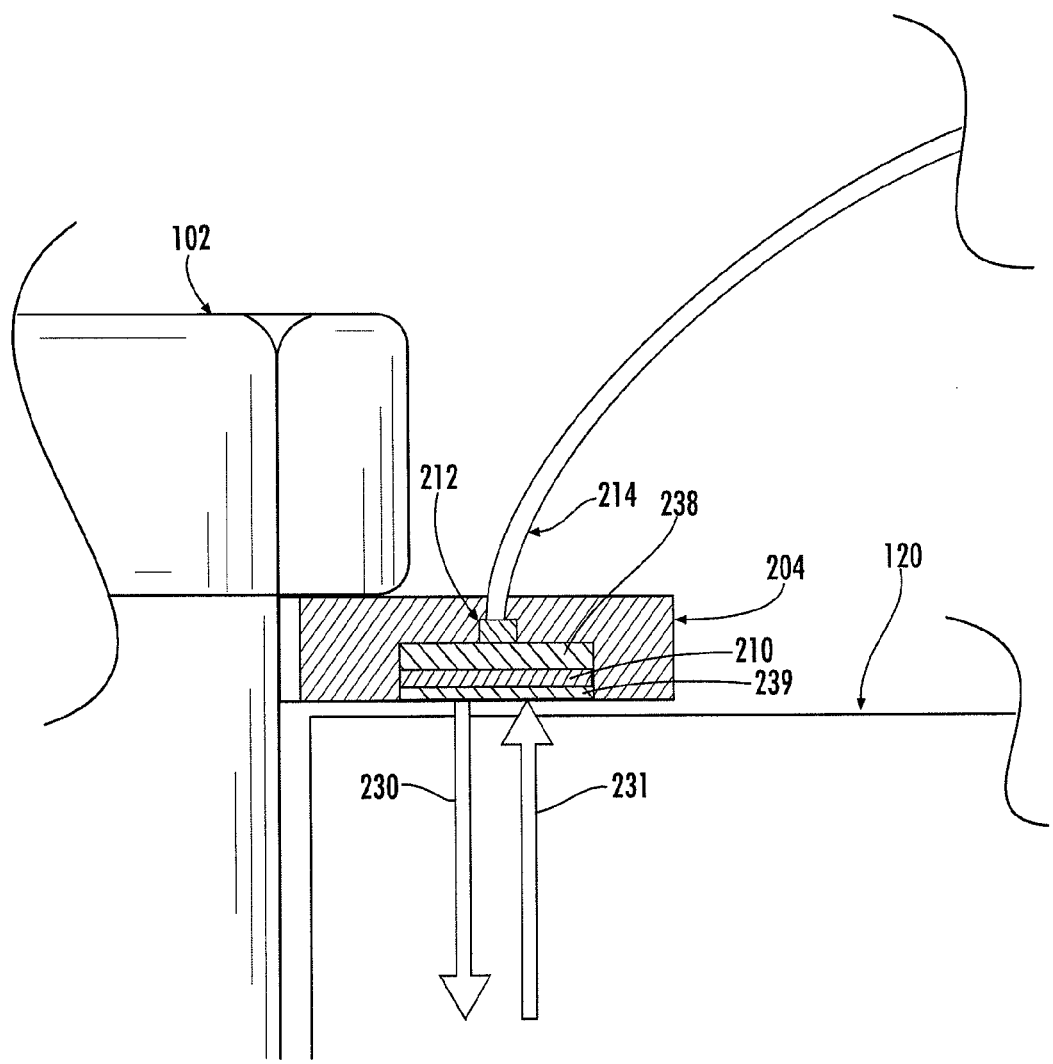
FIG. 2 is a cross-sectional schematic diagram of another embodiment of the present invention.
Figure 3:
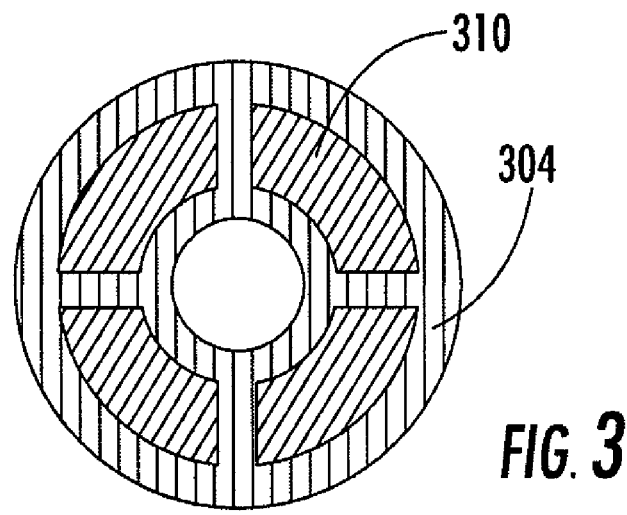
FIG. 3 is a plan view of yet another embodiment of the present invention.
Figure 4:
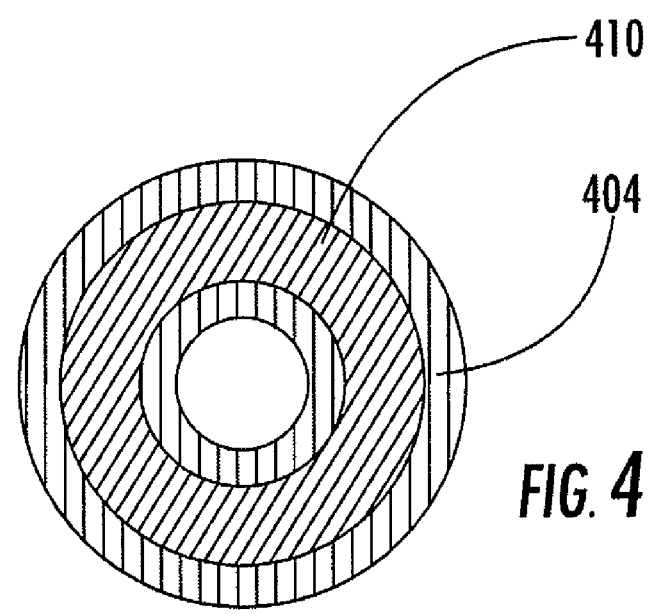
FIG. 4 is a plan view of yet another embodiment of the present invention.

FIG. 2 is an enlarged view of a cross-sectional schematic diagram of another embodiment of the present invention. By comparison to the embodiment of FIGS. 1 and 1A, the transducer 210 in the embodiment of FIG. 2 is located on the face of the washer 204 which is in contact with the structure 120, essentially with the transducer 210 between the washer 204 and the structure 120, rather than having the washer 104 between the transducer 110, 110A and the structure 120 as in the embodiment of FIGS. 1 and 1A. In the configuration of FIG. 2, the washer 204 becomes a casing or housing for the transducer 210, similar to how a typical transducer may have a steel sleeve or case. A damping material 238, such as a rubber, polymer, or rubber-like substance, may be placed behind the transducer to stop the crystal from ring-down or prolonged vibrating, thereby preventing the ring-down caused by one electrical impulse from interfering with the sound signal returning to the crystal before the next electrical impulse causes the crystal to ring again, and to fill any excess space in the cavity between a recess for a probe contact 212 and the transducer 210. An electrode lead wire 214 may run from the probe contact 212 through a small hole in the washer 204 to a data collection unit. An alternative embodiment may use wireless communications with an inspection sensor, thereby avoiding the need for a hole for a wire. The configuration of FIG. 2 permits the transducer 210 to be in direct contact with the structure 120 and avoids any interfering signals from washer 204. This configuration makes direct measurements of a structure possible without recourse to baseline subtractions. The configuration of FIG. 2 also permits the transducer to span through an area of the washer which may otherwise be beneath the head and/or bearing surface of a bolt where a transducer as in the embodiment of FIG. 1 could not be affixed because of potential damage to the transducer and/or physical interference between the bolt and the transducer. In the configuration of FIG. 2, the bearing load of the bolt may be transferred to the areas of the washer surfaces surrounding the transducer cavity, such as inner and outer perimeters and areas between segmented transducer crystals as shown in FIGS. 3 and 4, while leaving any cavities housing the transducer unaffected. To prevent damage to a transducer recessed in a cavity facing a surface of a structure, the transducer may be covered by a rubber or polymer contact facing 239. In such a manner, the transducer may "float" within the cavity between the contact facing 239 and the damping material 238. A similar cavity facing may be used to prevent damage to a transducer in embodiments of active washers where the transducer is recessed in the surface of the washer facing away from the structure and in contact with the head of the bolt. Because of the limited size for a transducer in the configuration of FIG. 2, an embodiment may advantageously use a MEMS transducer disposed in one or more cavities of a washer.

FIGS. 3 and 4 are plan views of embodiments for active washers in accordance with the present invention. The active washer of both FIGS. 3 and 4 are similar to the embodiment described with respect to FIG. 2 where the transducer is located on the surface of the washer facing the structure held together by the bolted joint, rather than on the surface of the washer facing the head of a bolt or a nut. The transducer may be manufactured as a segmented series, such as quadrants of piezoelectric crystals 310 recessed into four cavities in a washer 304, as shown in FIG. 3. Alternatively, a ring-shaped transducer 410 may be recessed into a single ring-shaped cavity in a washer 404, as shown in FIG. 4. Alternatively, an embodiment of the present invention may use multiple concentric ring-shaped cavities to enable a phasing functionality such as to make flaw length progression measurements. Similarly, a transducer affixed to the surface of a washer opposite a structure, as in a configuration like that of FIGS. 1 and 1A, may be segmented or ring-shaped, similar to the embodiments shown in FIGS. 3 and 4, and may be recessed into cavities, similar to the embodiments shown in FIGS. 2, 3, and 4 although on the opposite surface of the washer from the structure.

As with many other non-destructive inspection applications, various types of sensors may be used to perform different non-destructive inspection methods. For example, one embodiment of the present invention may use a single active washer with a pulse-echo transducer for one-sided inspection. An alternate embodiment of the present invention may use a pair of active washers on opposite surfaces of a bolted joint to perform through-transmission inspection.

If a bolted joint holds together multiple layers of a structure, a single active washer may inspect both layers of the structure in a pulse-echo inspection if a faying surface sealant or similar material is present between the multiple layers creating an interface layer, even though the interface layer may cause an interference reflection.

Data acquired by active washers can be used to detect defects or the onset of structural degradation so as to facilitate Condition-Based Maintenance and Vehicle Health Management techniques. Based on data from active washers, any necessary repairs may be made before defects worsen.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus for inspecting a structure, comprising:
   an active washer, comprising:
      a washer configured to at least partially surround a hole of a bolted joint structure and having a first side facing the structure; and
      an inspection sensor carried by the washer, wherein the inspection sensor is configured to inspect at least a portion of the structure proximate the first side of the washer by transmitting an ultrasonic longitudinal compression wave inspection signal from the inspection sensor into the structure.

2. The apparatus of claim 1, wherein the inspection sensor comprises a piezoelectric thin-film ceramic crystal.

3. The apparatus of claim 2, wherein the inspection sensor is disposed on the opposing side of the washer from the first side and further comprises a protective layer and a metal electrode layer, such that the protective layer is disposed between the metal electrode layer and the piezoelectric thin-film ceramic crystal.

4. The apparatus of claim 1, wherein the inspection sensor is configured to perform pulse-echo ultrasonic inspection by transmitting an ultrasonic inspection signal into the structure and receiving a reflected inspection signal from the structure.

5. The apparatus of claim 1, wherein the inspection sensor is configured to perform through-transmission ultrasonic inspection in cooperation with a corresponding inspection probe on the opposing surface of the structure from the inspection sensor.

6. The apparatus of claim 5, wherein the corresponding inspection probe comprises a second active washer configured to at least partially surround the hole of the bolted joint and having a first side facing the structure and a second inspection sensor carried by the second active washer, wherein the second inspection sensor is configured to inspect at least a portion of the structure proximate the first side of the second active washer.

7. The apparatus of claim 1, further comprising a fastener configured to be disposed through the washer and through the hole in the structure and configured to exert a load upon the washer and opposing surfaces of the structure whereby the fastener exerts a load against one of the surfaces of the structure by applying a load to the washer.

8. The apparatus of claim 7, wherein the fastener is a threaded bolt having a head and a shaft, and wherein the apparatus further comprises a threaded nut for screwing onto the threads of the bolt to exert a force load to the structure.

9. The apparatus of claim 8, further comprising a second active washer, and wherein the active washers are proximate opposing surfaces of the structure, one active washer disposed between the head of the bolt and a surface of the structure and the other active washer disposed between the nut and an opposing surface of the structure.

10. The apparatus of claim 1, wherein the washer defines at least one cavity in the first side of the washer facing the structure, and wherein the inspection sensor is disposed within the cavity.

11. The apparatus of claim 10, further comprising a dampening material disposed in the cavity such that the inspection sensor is located between the dampening material and the structure.

12. The apparatus of claim 10, further comprising a contact facing disposed between the inspection sensor and the structure, wherein the contact facing is attached to at least one of the inspection sensor, the cavity of the washer, and the first surface of the washer.

13. The apparatus of claim 10, wherein the washer further defines a probe contact recess in the cavity and a hole through the washer terminating at the probe contact recess for permitting a wired connection through the washer to the inspection sensor.

14. A method for performing remote inspection of a structure, comprising the steps of:
   providing a washer at least partially surrounding a hole of a bolted joint structure, wherein the washer has a first side facing the structure and has an inspection sensor carried by at least a portion of the washer, wherein the inspection sensor is configured inspect at least a portion of a structure proximate the first side of the washer;

transmitting an ultrasonic longitudinal compression wave inspection signal from the inspection sensor into the structure; and receiving the inspection signal from the structure.

15. The method of claim 14, wherein the step of receiving the inspection signal from the structure is performed by the inspection sensor operating in a pulse-echo mode of non-destructive inspection where the signal from the structure is a reflection of the inspection signal transmitted into the structure from the inspection sensor.

16. The method of claim 14, wherein the washer is a first washer and the inspection sensor is a first inspection sensor and the first washer is disposed proximate a first surface of the structure, the method further comprising the step of providing a second washer at least partially surrounding the hole of the bolted joint on an opposing second surface of the structure, wherein the second washer has a first side facing the second surface of the structure and has a second inspection sensor carried by at least a portion of the second washer, and wherein the first and second inspection sensors are configured to inspect at least a portion of the structure between the first sides of the washers by cooperating in a through-transmission non-destructive inspection, wherein the step of receiving the inspection signal from the structure is performed by the second inspection sensor.

17. The method of claim 14, wherein the steps of transmitting the inspection signal from the inspection sensor into the structure and receiving an inspection signal from the structure are performed periodically for monitoring a portion of the structure at the bolted joint.

18. The method of claim 14, wherein the inspection sensor is disposed on an opposing surface of the washer from the first side such that the step of transmitting an inspection signal from the inspection sensor into the structure requires the inspection signal to pass through the washer.

19. The method of claim 14, wherein the inspection sensor is disposed in at least one cavity defined in the first side of the washer such that the step of transmitting an inspection signal from the inspection sensor into the structure passes directly from the inspection sensor into the structure without passing through the washer.

20. An apparatus for inspecting a structure, comprising:
an active washer, comprising:
a washer configured to at least partially surround a hole of a bolted joint structure and having a first side facing the structure; and
an inspection sensor carried by the washer, wherein the inspection sensor is configured to inspect at least a portion of the structure proximate the first side of the washer, wherein the inspection sensor comprises at least two radially segmented transducer portions.

21. The apparatus of claim 20, wherein the inspection sensor comprises a series of radially segmented quarter transducer portions.

22. The apparatus of claim 20, wherein each radially segmented transducer portion of the inspection sensor is recessed in a respective cavity formed in the washer.

23. An apparatus for inspecting a structure, comprising:
an active washer, comprising:
a washer configured to at least partially surround a hole of a bolted joint structure and having a first side facing the structure; and
an inspection sensor carried by the washer, wherein the inspection sensor is configured to inspect at least a portion of the structure proximate the first side of the washer, wherein the inspection sensor comprises at least two concentric ring-shaped transducer portions.

24. The apparatus of claim 23, wherein each concentric ring-shaped transducer portion of the inspection sensor is recessed in a respective ring-shaped cavity formed in the washer.

25. The apparatus of claim 23, wherein the inspection sensor is configured to conduct phasing between the at least two concentric ring-shaped transducer portions to make flaw length progression measurements.

* * * * *